United States Patent [19]

Motoyama et al.

[11] Patent Number: 5,716,544
[45] Date of Patent: Feb. 10, 1998

[54] PHENYL ESTER COMPOUND AND LIQUID CRYSTAL COMPOSITION CONTAINING THE SAME

[75] Inventors: Yuki Motoyama; Tomoyuki Yui; Masahiro Johno; Takahiro Matsumoto; Teruyo Tomiyama, all of Tsukuba, Japan

[73] Assignee: Mitsubishi Gas Chemical Company, Inc., Tokyo, Japan

[21] Appl. No.: 635,320

[22] Filed: Apr. 19, 1996

[30] Foreign Application Priority Data

Apr. 21, 1995 [JP] Japan .................................. 7-096749
Jun. 12, 1995 [JP] Japan .................................. 7-144721

[51] Int. Cl.⁶ .......................... C09K 19/12; C09K 19/20
[52] U.S. Cl. .................... 252/299.65; 252/299.01; 252/299.64; 252/299.66; 252/299.67
[58] Field of Search .................... 252/299.01, 299.64, 252/299.65, 299.66, 299.67

[56] References Cited

U.S. PATENT DOCUMENTS

| | | | |
|---|---|---|---|
| 5,288,597 | 2/1994 | Hayashi | 430/448 |
| 5,364,560 | 11/1994 | Mizukami et al. | 252/299.65 |
| 5,534,190 | 7/1996 | Johno et al. | 252/299.65 |

OTHER PUBLICATIONS

CA51: 5310g. 1957.
A.D.L. Chandani, et al., "Tristable Switching in Surface Stablized . . . ", Jap. Journal of Appl. Physics, vol. 27, No. 5, pp. L729–L732 (May 1988).
M. Johno, et al., "Smectic Layer Switching by an Electric . . . ", Jap. Journal of Appl. Physics, vol. 28, No. 1, pp. L119–L120 (Jan. 1989).
A.D.L. Chandani, et al., "Novel Phases Exhibiting Tristable Switching", Jap. Journal of Applied Phys., vol. 28, No. 7, pp. L1261–L1264 (Jul. 1989).
A.D.L. Chandani, et al., "Antiferroelectric Chiral Smectic Phases . . . ", Jap. Journal of Applied Phys., vol. 28, No. 7, pp. L1265–L1268 (Jul. 1989).
M. Johno, et al., "Correspondence between Smectic Layer . . . ", Jap. Journal of Appl. Phys., vol. 29, No. 1, pp. L111–L114 (Jan. 1990).
N. Yamamoto, et al., "Full–Color Antiferroelectric Liquid . . . ", Preprints, 4th Int'l. Conf. on Ferroelectric Liquid Crystals Sep. 28–Oct. 1, 1993.

*Primary Examiner*—Shean C. Wu
*Attorney, Agent, or Firm*—Sherman and Shalloway

[57] ABSTRACT

A phenyl ester compound of the following general formula (1),

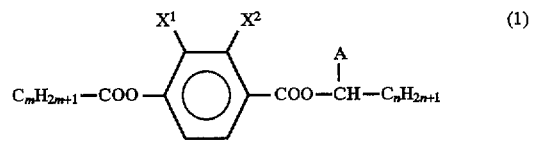

wherein m is an integer of 3 to 8, n is an integer of 3 to 11, both of $X^1$ and $X^2$ are hydrogen atoms, or one of $X^1$ and $X^2$ is a fluorine atom and the other is a hydrogen atom, and A is a hydrogen atom or —$CH_3$; and an anti-ferroelectric liquid crystal composition containing the above phenyl ester compound and a specific anti-ferroelectric liquid crystal compound or a specific liquid crystal compound having ferrielectric-phase.

18 Claims, 1 Drawing Sheet

⊙ : UP STATE ON THE PLANE
⊗ : DOWN STATE ON THE PLANE

PHENYL ESTER COMPOUND AND LIQUID CRYSTAL COMPOSITION CONTAINING THE SAME

FIELD OF THE INVENTION

The present invention relates to a novel phenyl ester compound, and a novel anti-ferroelectric liquid crystal composition containing the phenyl ester compound, a novel ferrielectric liquid crystal composition containing the phenyl ester compound and liquid crystal display devices for which these compositions are adapted.

PRIOR ART OF THE INVENTION

A liquid crystal display device has been so far applied to various small-sized display devices owing to its low-voltage operability, low power consumption and thin display. With recent broadening of application and use of liquid crystal display devices to/in an information and office automation-related machine and equipment field and a television field, there are rapidly growing demands for high-performance, large-sized liquid crystal display devices having higher display capacity and higher display quality over existing CRT display devices.

That is, a liquid crystal display device is required to achieve an increased display capacity, full-color display, a wide viewing angle, a high response and a high contrast. As a liquid crystal display mode (liquid crystal driving method) for complying with these requirements, available at present are a simple matrix driven super twisted nematic (STN) liquid crystal display device using a nematic liquid crystal material and an active matrix driven thin film transistor (TFT) or diode (MIM) liquid crystal display device.

With regard to the above display modes, the problems which are recently pointed out are that the response speed is slow and that the viewing angle is narrow.

That is, the response speed is on the order of several tens in terms of microsecond and no good display quality can be obtained for the video frame rate display. Further, the viewing angle is necessarily narrow since the display uses a twisted state (twisted alignment) of liquid crystal molecules. In gray-scaling in particular, the viewing angle is sharply narrowed, and a contrast ratio and a color are altered from some viewing angles.

Every efforts are being made to overcome the above problems, while it is difficult to reach a fundamental resolution so long as a nematic liquid crystal is used. At present, therefore, no display quality over that of a CRT is achieved. Thus, a nematic liquid crystal display device can not meet the demand for the high performance, large-sized liquid crystal display device.

Under the circumstances, a liquid crystal display device for which a ferroelectric liquid crystal is adapted is attracting attention as a high-response liquid crystal display device having a wide viewing angle. A surface stabilized ferroelectric liquid crystal (SSFLC) device disclosed by Clark and Lagerwall attracts attention in that it has a fast response and a wide viewing angle. Its switching characteristics have been studied in detail, and a number of ferroelectric liquid crystals have been synthesized for optimizing various physical property. However, it has problems in that its threshold characteristic is insufficient, that its contrast is low since its layer has a chevron structure, that no fast response is accomplished, that alignment control is difficult so that it is not easy to accomplish the bistability which is one of the greatest characteristics of SSFLC, and that alignment destroyed by mechanical shock is difficult to restore. It is therefore required to overcome these problems for its practical use.

In addition to the above, the development of devices having switching mechanisms different from that of SSFLC are also under way.

Switching among tristable states of a liquid crystal substance having an anti-ferroelectric phase (to be referred to as "anti-ferroelectric liquid crystal substance" hereinafter) is also one of these new switching mechanisms (Japanese Journal of Applied Physics, Vol. 27, pp. L729, 1988).

An anti-ferroelectric liquid crystal device has three stable states, i.e., two uniform states (Ur, Ul) observed in a ferroelectric device and a third state. Chandani et al reports that the above third state is an anti-ferroelectric phase (Japanese Journal of Applied Physics, vol. 28, pp. L1261, 1989, Japanese Journal of Applied Physics, vol. 28, pp. L1265, 1989).

The above switching among tristable states is the first characteristic of an anti-ferroelectric liquid crystal device. The second characteristic of the anti-ferroelectric liquid crystal device is that a sharp threshold value is present relative to an applied voltage. Further, it has a memory effect, which is the third characteristic of the anti-ferroelectric liquid crystal device.

By utilizing these excellent characteristics, a simple matrix-driven liquid crystal display device having a fast response speed and a good contrast can be achieved.

The anti-ferroelectric liquid crystal has another great characteristic in that its layer structure easily performs switching when an electric field is applied (Japanese Journal of Applied Physics, Vol. 28, pp. L119, 1989, Japanese Journal of Applied Physics, vol. 29, pp. L111, 1990).

On the basis thereof, a liquid crystal display device free of defects and capable of self-restoring alignment can be produced, and a liquid crystal device having an excellent contrast can be achieved.

Further, it has been demonstrated that analogue gradation caused by applied voltage which is almost impossible for a ferroelectric liquid crystal is possible for an anti-ferroelectric liquid crystal. Accordingly, it is made possible to shift toward a full-color display, and the importance of an anti-ferroelectric liquid crystal is increasing (Preprints of No. 4 Ferroelectric Liquid Crystal International Symposium, page 77, 1993).

As described above, an anti-ferroelectric liquid crystal is gaining reliable dominance, while it is desired to broaden a driving temperature range and further improve its response speed, and it is further desired to develop an anti-ferroelectric liquid crystal having a smectic A phase.

With regard to the response speed, there is a serious problem on a low-temperature side, particularly on the side of temperatures lower than room temperature. Practically, the response speed on a low-temperature side, e.g., at 10° C., is as low as $\frac{1}{10}$ to $\frac{1}{20}$ of that at room temperature. Attempts are therefore being made to change frequency or a driving voltage or to install a heater for the purpose of making the driving smoother on a low-temperature side.

However, changing the frequency or the voltage has its limitation, and the changing of the frequency or the voltage has not yet enough compensated the poor characteristics of the liquid crystal. Further, when a heater is installed, the device shows a decrease in transmittance so that the contrast decreases. As a result, a device having a high display quality can be no longer obtained.

For an anti-ferroelectric liquid crystal, there are two switching processes, one from an anti-ferroelectric state to a ferroelectric state and the other from a ferroelectric state to an anti-ferroelectric state. The speeds of these two switchings processes based on voltage, i.e., response speed, are important factors for determining a display quality.

The response speed particularly from an anti-ferroelectric state to a ferroelectric state (to be referred to as "response speed I" hereinafter) is important since it is, for example, an addressing speed multiplexing driving so that it determines the number of scanning lines which constitute one frame. That is, as the response speed increases, the number of scanning lines can be increased, so that a high-resolution device can be achieved.

Further, concerning the response speed from a ferroelectric state to an anti-ferroelectric state (to be referred to as "response speed II" hereinafter), a required speed alters depending upon a design of a driving method of the device. For example, it alters by the set voltage of an offset voltage. However, when the response speed II is too fast, a ferroelectric state can not be fully maintained (a light or dark state cannot be maintained). When it is too slow, disadvantageously, no change from a ferroelectric state to an anti-ferroelectric state takes place (no rewriting from a light or dark state to a dark or light state can be performed).

That is, in the response speed II, an optimum response speed is set after a drive method is determined.

As explained above, a fast response speed I is important for achieving a high-resolution device, and at the same time, it is preferred that the dependency of the response speed on temperature be low.

On the other hand, an active matrix (AM) driving at least requires a liquid crystal material which can be driven at a voltage of 10 V or lower, and it is difficult to drive a display device of the above anti-ferroelectric liquid crystal at a low voltage since the anti-ferroelectric liquid crystal generally has a high threshold voltage. Further, the anti-ferroelectric liquid crystal has another problem in that gray-scaling is difficult since the optical response thereof has a hysterisis (slow optical response).

A liquid crystal compound having a ferrielectric phase is conceivable as a material which can overcome the above problems and can be suitably adapted for AM driving.

A liquid crystal compound having a ferrielectric phase (=SCγ*) was first found in 4-(4-octyloxyphenyl)benzoic acid-4-(1-methylheptyloxycarbonyl)phenyl (called "MHPOBC" for short) in 1989 (Japanese Journal of Applied Physics, Vol. 29, No. 1, 1990, pages L131–137).

MHPOBC has the formula of

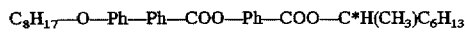

in which Ph is 1,4-phenylene, C* is asymmetric carbon and each alkyl is linear.

The phase sequence of the above compound is as follows.

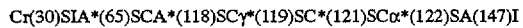

in which Cr is a crystal phase, SIA* is a chiral smectic IA phase, SCA* is a chiral smectic CA phase (anti-ferroelectric phase), SCγ* is a chiral smectic Cγ phase (ferrielectric phase), SC* is a chiral smectic C phase (ferroelectric phase), SCα* is a chiral smectic Cα phase, SA is a smectic A phase, I is an isotropic phase, and parenthesized figures show phase transition temperatures (°C.).

BRIEF DESCRIPTION OF DRAWINGS

For explaining the state of a liquid crystal in a ferrielectric phase, FIG. 1 shows a molecular arrangement state in a ferrielectric phase, and FIG. 2 shows an optical response of a ferrielectric phase to a triangular wave.

Figure 1:
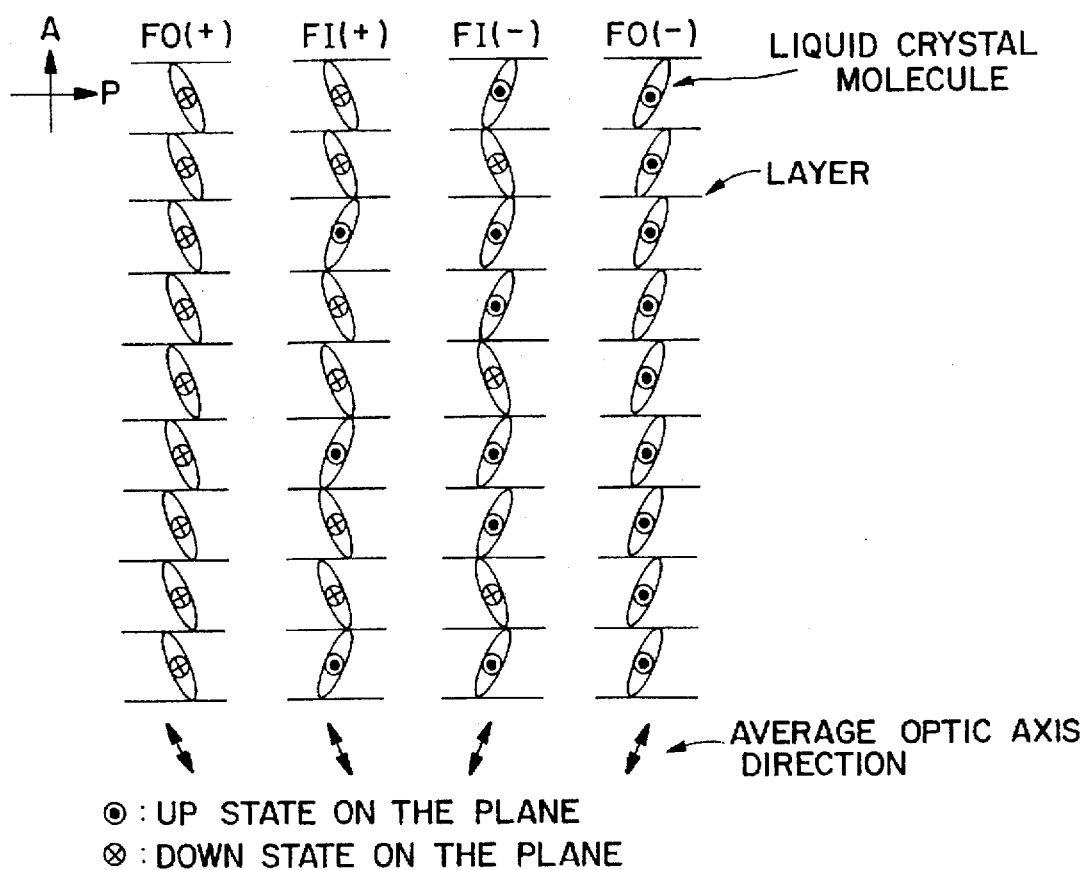
FIG. 1 shows a molecular arrangement state in a ferrielectric phase, in which FI(+) and FI(−) are ferrielectric states and FO(+) and (FO(−) are ferroelectric states.

The ferrielectric phase has a molecular arrangement FI(+) (when applied voltage is positive) or a molecular arrangement FI(−) (when applied voltage is negative) as shown in FIG. 1. In a state where no electric field is present, it is assumed that FI(+) and FI(−) are co-present since FI(+) and FI(−) are equivalent.

An average optic axis is therefore in a layer normal, and a dark state is brought under the position of polarizers shown in FIG. 1.

Figure 2:
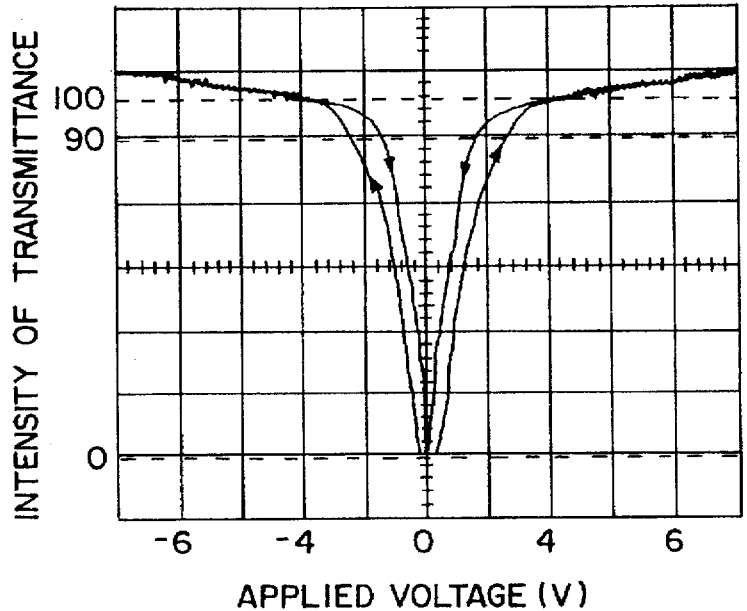
FIG. 2 shows an optical response of a ferrielectric phase of MHPOBC to a triangular wave.

The above state corresponds to a site where an applied voltage is 0 and the intensity of transmittance is 0 in FIG. 2.

Further, each of FI(+) and FI(−) has spontaneous polarization as is clear in molecular arrangement states, and when these are co-present, the spontaneous polarizations are cancelled, which causes an average spontaneous polarization of zero. Like an anti-ferroelectric phase, the ferrielectric phase is therefore free from an image sticking phenomenon.

As an electric field is applied to a ferrielectric phase, a domain having an extinguished position appears at a voltage lower than that at which a ferroelectric state is reached. This domain shows that a ferrielectric phase has an optic axis in a direction tilted apart from a layer normal although it is not so tilted as that in a ferroelectric state.

The above intermediate state is considered to be FI(+) or FI(−).

In the above case, not a continuous change but a stepwise change in the intensity of transmittance could have been observed between voltages 0V and 4V in FIG. 2. In FIG. 2, however, a continuous intensity of transmittance was observed. This is presumably because the threshold voltage of FI(+)→FO(+) or FI(−)→FO(−) is not clear.

In the present invention, a liquid crystal phase in which the above intermediate state is always observed refers to a ferrielectric phase, and a liquid crystal of which said phase is the broadest temperature range refers to a ferrielectric liquid crystal.

When the applied voltage is further increased, the ferrielectric phase causes phase transition to a ferroelectric phase FO(+) or FO(−) which is a stabilized state depending upon a direction of an electric field. That is, in FIG. 2, a phase in which the intensity of transmittance is brought into a saturated state (left and right flat portions in FIG. 2) is FO(+) or FO(−).

It is seen in FIG. 1 that the above ferroelectric state FO(+) or FO(−) causes a greater spontaneous polarization than the ferrielectric state FI(+) or FI(−).

As explained above, the ferrielectric phase can be used as follows; A state where FI(+) and FI(−) are co-present is "dark", and ferroelectric states FO(+) and FO(−) are "light".

A conventional ferroelectric liquid crystal permits switching between FO(+) and FO(−), while a ferrielectric phase has a major characteristic feature in that it permits switching among four states, FI(+), FO(+), FO(−) and FI(−).

Meanwhile, the principle of each liquid crystal display uses birefringence of liquid crystal, and a display device of which the viewing angle dependency is small can be fabricated.

As shown in FIG. 2, a ferrielectric phase has a small difference between the voltage required for a change from a ferrielectric state to a ferroelectric state and the voltage required for a change from a ferroelectric state to a ferrielectric state. That is, a ferrielectric phase has a strong tendency that the width of its hysterisis is narrow, and the ferrielectric phase is characteristically suitable for AM driving and gray-scaling in AM driving.

Further, in a change based on voltage, a ferrielectric phase has a tendency that the threshold voltage for a change from a ferrielectric state to a ferroelectric state is smaller than that of an anti-ferroelectric phase, which also proves that the ferrielectric phase is a liquid crystal phase suitable for AM driving.

Problems that the Invention Intends to Solve

In the anti-ferroelectric liquid crystal, the faster response speed is required on a low-temperature side, the temperature range of the anti-ferroelectric phase is required to broaden, and a smectic A phase is required to be present, as described above.

M. Nakagawa has shown that the response speed of an anti-ferroelectric liquid crystal depends upon the rotation viscosity of liquid crystal molecules (Masahiro Nakagawa, Japanese Journal of Applied Physics, 30, 1759 (1991)). That is, with a decrease in viscosity, the response speed increases.

Further, when the response speed relative to temperature is observed, the response speed starts to become slow around room temperature and exponential-functionally becomes slow in the temperature range lower than room temperature. An anti-ferroelectric liquid crystal has a high viscosity since its liquid crystal phase is a smectic phase, so that its viscosity sharply increases on a low-temperature side, and it is considered that the response speed sharply becomes slow due to the viscosity resistance thereof.

In one specific method for overcoming the above problem, it is conceivable to make an attempt to add a compound having a relatively low viscosity to a liquid crystal composition to decrease the viscosity of the composition as a whole so as to improve the response speed, and this method is considered the most practical solution at present. However, this method tends to drop the upper limit temperature of the anti-ferroelectric phase, and it poses a problem in respect of the temperature range of the anti-ferroelectric phase although the response speed is improved. When an anti-ferroelectric liquid crystal device is considered to be used as a display, the device has a temperature of at least about 40° C. due to heat of backlight. For normal driving of the device, therefore, the upper-limit temperature of the anti-ferroelectric phase is required to be at least 40° C., preferably at least 50° C. And, a smectic A phase is required to exist on the side of a temperature higher than this temperature for obtaining excellent alignment. Further, on the low-temperature side, the device is at least required to be driven at 10° C. The lower-limit temperature of the anti-ferroelectric phase is at least required to be 0° C.

The present invention has been made from the above point of view, and according to the present invention, there is provided an anti-ferroelectric liquid crystal composition which has an anti-ferroelectric phase in a wide temperature range, which has a smectic A phase and which exhibits rapid response at a low temperature.

According to the present invention, similarly, there is provided a ferrielectric liquid crystal composition which contains a liquid crystal compound having a ferrielectric phase suitable for AM driving, which has a ferrielectric phase in a wide temperature range, which has a smectic A phase, which exhibits rapid response at a low temperature and which has no hysterisis and has a low threshold voltage.

Means for Solving the Problems

That is, according to the present invention, there is provided a phenyl ester compound of the following general formula (1),

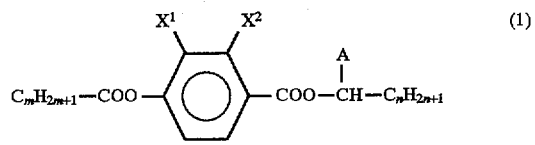

wherein m is an integer of 3 to 12, n is an integer of 1 to 11, both of $X^1$ and $X^2$ are hydrogen atoms, or one of $X^1$ and $X^2$ is a fluorine atom and the other is a hydrogen atom, and A is a hydrogen atom or —$CH_3$.

According to the present invention, further, there is provided an anti-ferroelectric liquid crystal composition containing a phenyl ester compound of the general formula (1) and an anti-ferroelectric liquid crystal compound of the general formula (2),

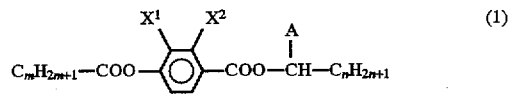

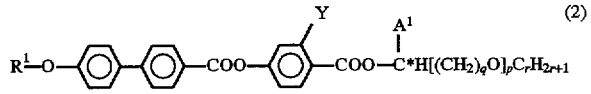

wherein, in the general formula (1), m is an integer of 3 to 12, n is an integer of 1 to 11, both of $X^1$ and $X^2$ are hydrogen atoms, or one of $X^1$ and $X^2$ is a fluorine atom and the other is a hydrogen atom, and A is a hydrogen atom or —$CH_3$, and in the general formula (2), $R^1$ is a linear alkyl group having 4 to 12 carbon atoms, Y is a hydrogen atom or a fluorine atom and $A^1$ is —$CH_3$ or —$CF_3$, provided that when $A^1$ is —$CH_3$, p is 0 and r is an integer of 6 to 10, that when $A^1$ is —$CF_3$, p is 0 and r is an integer of 6 to 8, or that when $A^1$ is —$CF_3$, p is 1, q is an integer of 5 to 8 and r is 2 or 4.

Further, according to the present invention, there is provided a ferrielectric liquid crystal composition containing a phenyl ester compound of the general formula (1) and a liquid crystal compound having ferrielectric-phase of the general formula (3),

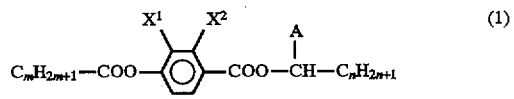

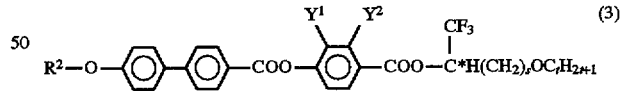

wherein, in the general formula (1), m is an integer of 3 to 12, n is an integer of 1 to 11, both of $X^1$ and $X^2$ are hydrogen atoms, or one of $X^1$ and $X^2$ is a fluorine atom and the other is a hydrogen atom, and A is a hydrogen atom or —$CH_3$, and in the general formula (3), $R^2$ is a linear alkyl group having 7 to 12 carbon atoms, both $Y^1$ and $Y^2$ are hydrogen atoms or one of $Y^1$ and $Y^2$ is a fluorine atom and the other is a hydrogen atom, s is an integer of 2 to 4 and t is an integer of 2 to 4.

The phenyl ester compound of the general formula (1) provided by the present invention preferably has no liquid crystal phase when A is a hydrogen atom. Further, when A is —$CH_3$, n is preferably an integer of 4 to 8.

In the anti-ferroelectric liquid crystal of the general formula (2) in the anti-ferroelectric liquid crystal composition provided by the present invention, preferably, $R^1$ is a linear alkyl group having 6 to 10 carbon atoms and Y is a fluorine atom.

Further, in the general formula (2), preferably, $A^1$ is —$CH_3$, p is 0 and r an integer of 6 to 10. Further, in the general formula (2), preferably, $A^1$ is —$CF_3$, p is 1 and q is an integer of 5 to 8, the most preferably, 5. In this case, further, r is the most preferably 2.

Further, preferably, $A^1$ is —$CF_3$, p is 0 and r is an integer of 6 to 8.

In the anti-ferroelectric liquid crystal composition, the content of the phenyl ester compound of the general formula (1) is 1 to 50 mol %, preferably 1 to 30 mol %. Practically, the anti-ferroelectric liquid crystal composition is required to have a smectic A phase. When smectic A phase is not contained, the alignment is not obtained and hence, it is difficult to achieve a high contrast.

The temperature range of the anti-ferroelectric phase is preferably as wide as possible. The transition temperature on a high-temperature side is preferably at least 40° C., and the transition temperature on a low-temperature side is preferably 0° C. or lower.

The anti-ferroelectric liquid crystal composition of the present invention can be formed into a simple matrix driven liquid crystal display device which can be driven in a wide temperature range, by providing it between a pair of glass plates installed with electrodes.

In the ferrielectric liquid crystal composition of the present invention, preferred are a liquid crystal compound of the general formula (3) in which s is 4, t is an integer of 2 to 4 and $R^2$ is a linear alkyl group having 7 to 12 carbon atoms; a liquid crystal compound of the general formula (3) in which s is 3, t is an integer of 2 to 4 and $R^2$ is a linear alkyl group having 9 to 12 carbon atoms; and a liquid crystal compound of the general formula (3) in which s is 2, t is 2 and $R^2$ is a linear alkyl group having 8 or 9 carbon atoms.

In the ferrielectric liquid crystal composition of the present invention, the content of the phenyl ester compound of the general formula (1) is i to 40 mol %, preferably 10 to 30 mol %. In particular, the ferrielectric liquid crystal composition exhibiting a ferrielectric phase in the temperature range of from 0° C. to 40° C., preferably in the range of from 0° C. to 50° C. is preferred.

The threshold voltage at which the above ferrielectric liquid crystal composition changes from a ferrielectric phase to a ferroelectric phase is preferably 5 V/μm or smaller, particularly preferably 3 V/μm or smaller.

The ferrielectric liquid crystal composition of the present invention is sandwiched between glass plates installed with non-linear active elements such as thin film transistors or diodes provided for each of pixels, whereby an active matrix liquid crystal display device which can be driven in a wide temperature range can be provided. And, the active matrix liquid crystal device can be used as one in which the driving of a liquid crystal by a voltage with non-linear active elements is performed by switching among two ferrielectric states, two ferroelectric states and intermediate states therebetween.

The anti-ferroelectric liquid crystal compound of the general formula (2) and the ferrielectric-phase-possessing liquid crystal compound of the general formula (3), used in the present invention, can be easily produced by the method disclosed by the present inventors (Japanese Laid-open Patent Publication No. 4-198155.)

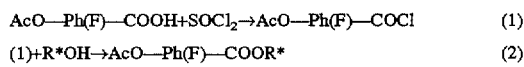

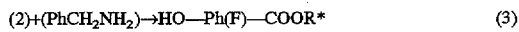

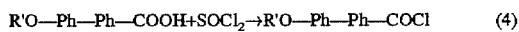

In the above reaction scheme, Ac is a $CH_3CO$— group, Ph is a 1,4-phenylene group, Ph(F) is a 1,4-phenylene group which may have a fluorine atom substituted on its 2- or 3-position, R* is an optically active alcohol residue and R' is a linear alkyl group.

The above production method is briefly explained below.

(1) p-Acetoxybenzoic acid substituted or not-substituted with fluorine is chlorinated with thionyl chloride.

(2) The chlorinated product (1) and an optically active alcohol are allowed to react to form an ester.

(3) The ester (2) is deacetylated.

(4) Alkyloxybiphenylcarboxylic acid is chlorinated.

(5) The phenol (3) and chlorinated product (4) are allowed to react to form a liquid crystal.

[Effect of the Invention]

The present invention provides a novel phenyl ester compound, an anti-ferroelectric liquid crystal composition containing the phenyl ester compound and a ferrielectric liquid crystal composition containing the phenyl ester compound.

The novel anti-ferroelectric liquid crystal composition provided by the present invention has an anti-ferroelectric phase in a wide temperature range, exhibits a fast response, and therefore can provide an anti-ferroelectric liquid crystal display device having a high display quality. Further, the novel ferrielectric liquid crystal composition provided by the present invention has a ferrielectric phase in a wide temperature range, exhibits a fast response, has no hysterisis and therefore can provide an active matrix liquid crystal display device having a high display quality.

[EXAMPLES]

The present invention will be further specifically explained with reference to Examples and Comparative Examples hereinafter, while the present invention shall not be limited to these Examples.

Example 1

Preparation of heptyl 4-decanoyloxy-2-fluorobenzoate (m=9, n=7, A=H, $X^1$=H, $X^2$=F in the formula (1) (E1))

(1) Preparation of 4-decanoyloxy-2-fluorobenzoic Acid 15.6 Grams (0.1 mol) of 4-hydroxy-2-fluorobenzoic acid was dissolved in 140 ml of dichloromethane. To this solution were consecutively added 16 ml of triethylamine, 20.1 g (0.11 mol) of n-decanoic acid chloride and 0.97 g (0.0079 mol) of dimethylaminopyridine, and the mixture was stirred at room temperature for a whole day and night. To this was added 50 ml of 10% hydrochloric acid, and the mixture was extracted with 100 ml of ether three times. An organic layer was washed with 100 ml of a sodium chloride aqueous solution three times, and then dried over anhydrous sodium sulfate. The solvent was distilled off, and then the residue was washed with 400 ml of hexane to give 25.5 g (yield 82%) of the intended product.

(2) Preparation of heptyl 4-decanoyloxy-2-fluorobenzoate

Thionyl chloride (10 ml) was added to 0.5 g (0.0016 mol) of the 4-decanoyloxy-2-fluorobenzoic acid obtained in (1), and the mixture was refluxed under heat for 4 hours. The thionyl chloride was distilled off, and 0.53 g of the resultant acid chloride was dissolved in toluene. To this solution were consecutively added 0.18 g (0.0015 mol) of n-heptanol and 0.27 g (0.0034 mol) of pyridine, and the mixture was stirred at room temperature for 24 hours. To this mixture was added 10 ml of water, and the mixture was stirred for 30 minutes. Then, 20 ml of 1N hydrochloric acid was added, and the mixture was extracted with 20 ml of dichloromethane twice. An organic layer was washed with 20 ml of water and then dried over anhydrous sodium sulfate. The solvent was distilled off to give 0.68 g of a crude product. The crude product was subjected to silica gel column chromatography to give 0.48 g (yield 76%) of the end product.

The NMR data and chemical formula of the end product are shown later.

Liquid crystal phases were identified by texture observation and DSC (differential scanning calorimeter). No liquid crystal phase was found in the compound obtained in this Example. The following Table 1 shows the melting point (solidifying point) of the compound.

Examples 2–19

Phenyl ester compounds of the general formula (1) in which m, n, A, $X^1$ and $X^2$ are as shown in Table 1 were synthesized in the same manner as in Example 1.

The so-obtained phenyl ester compounds were analyzed and identified in the same manner as in Example 1. No liquid crystal phase was found in the compounds obtained in Examples 2 to 19. Table 1 shows the melting points (solidifying points) of the compounds.

TABLE 1

| Example No. | 1 | 2 | 3 | 4 | 5 | 6 | 7 | 8 | 9 | 10 |
|---|---|---|---|---|---|---|---|---|---|---|
| m | 9 | 3 | 4 | 5 | 7 | 10 | 5 | 5 | 7 | 9 |
| n | 6 | 6 | 6 | 6 | 8 | 2 | 2 | 4 | 4 | 8 |
| A | H | H | H | H | H | H | H | H | H | H |
| $X^1$ | H | H | H | H | H | H | H | H | H | H |
| $X^2$ | F | F | F | F | F | F | F | F | F | F |
| Melting point (°C.) | −1 | <−50 | <−50 | −40 | −26 | −1 | −27 | −35 | −19 | −3 |
| Compound No. | E1 | E2 | E3 | E4 | E5 | E6 | E7 | E8 | E9 | E10 |

| Example No. | 11 | 12 | 13 | 14 | 15 | 16 | 17 | 18 | 19 |
|---|---|---|---|---|---|---|---|---|---|
| m | 9 | 10 | 5 | 9 | 3 | 10 | 5 | 9 | 9 |
| n | 10 | 10 | 4 | 8 | 2 | 8 | 4 | 5 | 6 |
| A | H | H | H | H | H | H | H | $CH_3$ | $CH_3$ |
| $X^1$ | H | H | F | H | H | H | H | H | H |
| $X^2$ | F | F | H | H | F | F | H | F | F |
| Melting point (°C.) | 6 | 8 | <−50 | 12 | <−50 | 27 | <−50 | <−50 | <−50 |
| Compound No. | E11 | E12 | E13 | E14 | E15 | E16 | E17 | E18 | E19 |

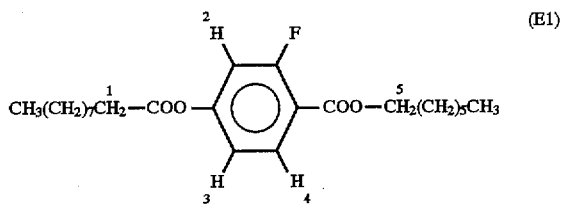

(E1)

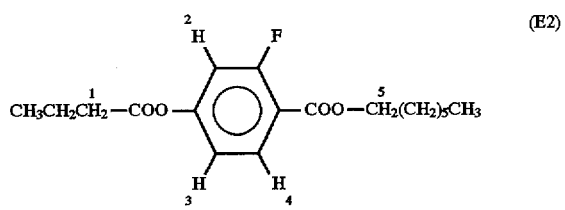

(E2)

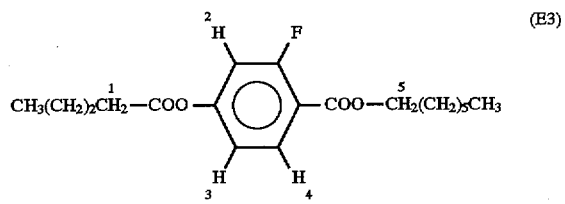

(E3)

TABLE 1-continued
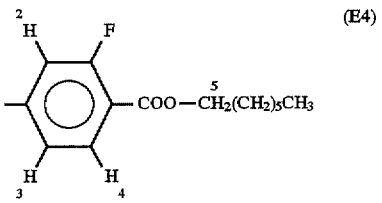
(E4)
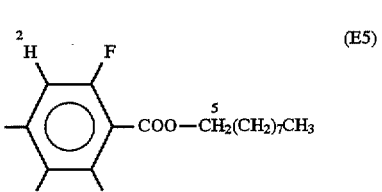
(E5)
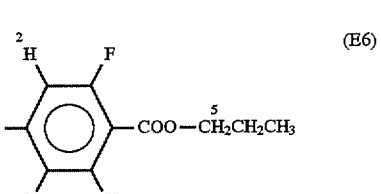
(E6)
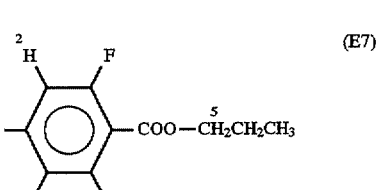
(E7)
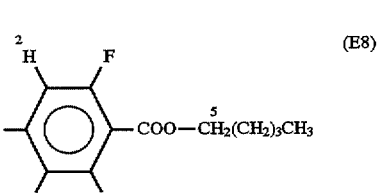
(E8)
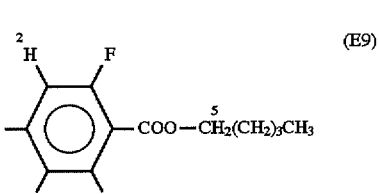
(E9)
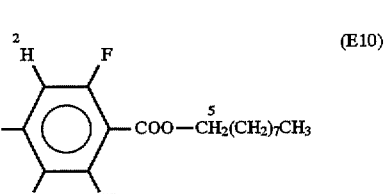
(E10)

TABLE 1-continued
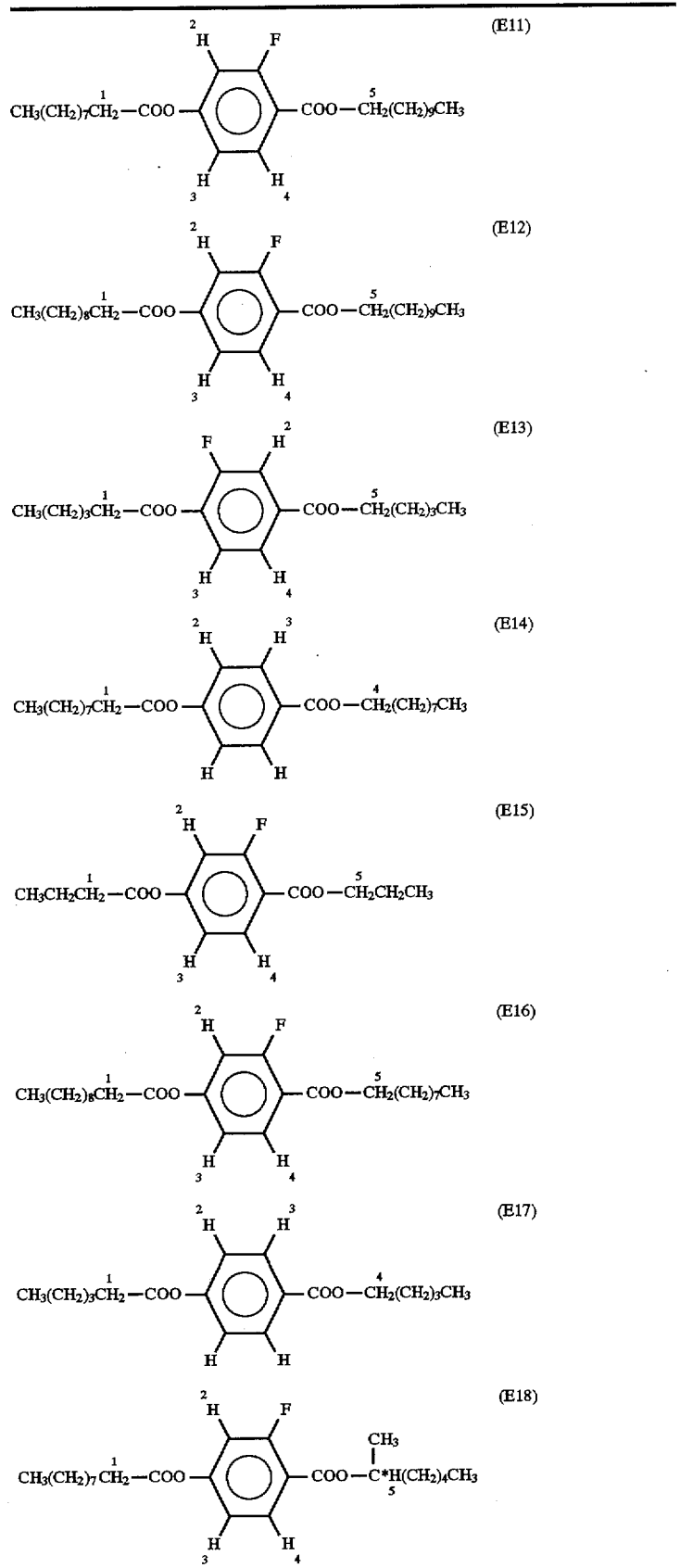

TABLE 1-continued

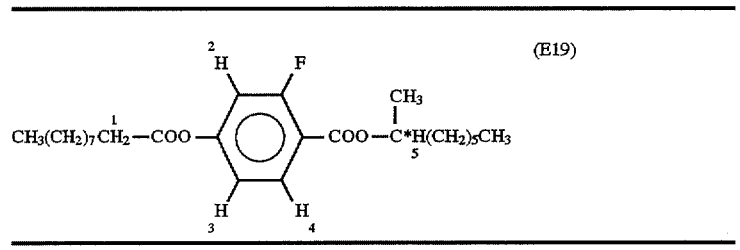

TABLE 2

| Hydrogen atom No. | 1 | 2 | 3 | 4 | 5 |
|---|---|---|---|---|---|
| E1–12,15,16 (ppm) | 2.6 | 7.0 | 7.0 | 8.0 | 4.4 |
| E13 | 2.6 | 7.8 | 7.2 | 7.8 | 4.4 |
| E14,17 | 2.6 | 7.2 | 8.1 | 4.4 | |
| E18 | 2.6 | 6.9 | 6.9 | 8.0 | 5.2 |
| E19 | 2.6 | 7.0 | 7.0 | 8.0 | 5.2 |

Example 20

The following anti-ferroelectric liquid crystal (2A) was mixed with 20 mol % of the phenyl ester compound (E1) obtained in Example 1 to obtain an anti-ferroelectric liquid crystal composition. The anti-ferroelectric liquid crystal composition was identified for phases and measured for a response time. Table 3 shows the results.

$C_9H_{19}$—O—Ph—Ph—COO—Ph(3F)—COO—
$C*H(CF_3)(CH_2)_5OC_2H_5$                                                 2A ($R^1=C_9H_{19}$, Y=F, $A^1=CF_3$, p=1, q=5, r=2 in the formula 2)

The liquid crystal 2A had no smectic A phase, while a composition having a smectic A phase was obtained by mixing it with E1. The composition had an anti-ferroelectric phase in a wide temperature range, and the response time I was greatly improved.

The composition was identified for phases by texture observation and DSC (differential scanning calorimeter).

The response time was measured as follows.

A liquid crystal cell (cell thickness 1.8 µm) having a rubbed polyimide thin film and ITO electrodes was charged with the liquid crystal composition in an isotropic state. The cell was gradually cooled at a rate of 1° C./minute to align the liquid crystal in a smectic A (SA phase). The cell was placed between crossed polarizers with the one polarier in parallel with the layer direction.

A step voltage of 50 V at a frequency of 10 Hz was applied to the liquid crystal cell. The time required for a transmission change from 10% to 90% was defined as a response time.

Examples 21–33

The same anti-ferroelectric liquid crystal as the anti-ferroelectric liquid crystal (2A) was mixed with 20 mol % each of the phenyl ester compounds (E2–E14) obtained in Examples 2 to 14 to obtain anti-ferroelectric liquid crystal compositions. The so-obtained compositions were measured for physical properties, etc., and Table 3 shows the results.

TABLE 3

| | Compound | | Response time | | |
|---|---|---|---|---|---|
| | Symbol/Mole % | Phase sequence | I | II | temperature |
| Liquid crystal 2A | | I(83)SC*(77)SCA*(<–50)Cr | 79 | 2020 | 10° C. |
| Example 20 | E1/20 | I(64)SA(56)SCA*(<–20)Cr | 47 | 5500 | 10 |
| Example 21 | E2/20 | I(65)SA(56)SCA*(<–20)Cr | 40 | 2160 | 10 |
| Example 22 | E3/20 | I(64)SA(53)SCA*(<–20)Cr | 34 | 4000 | 10 |
| Example 23 | E4/20 | I(63)SA(52)SCA*(<–20)Cr | 36 | 9500 | 10 |
| Example 24 | E5/20 | I(66)SA(58)SCA*(<–20)Cr | 50 | 9500 | 10 |
| Example 25 | E6/20 | I(64)SA(56)SCA*(<–20)Cr | 47 | 8500 | 10 |
| Example 26 | E7/20 | I(68)SA(55)SCA*(<–20)Cr | 37 | 5500 | 10 |
| Example 27 | E8/20 | I(66)SA(54)SCA*(<–20)Cr | 34 | 6600 | 10 |
| Example 28 | E9/20 | I(64)SA(56)SCA*(<–20)Cr | 44 | 7800 | 10 |
| Example 29 | E10/20 | I(64)SA(55)SCA*(<–20)Cr | 52 | 9800 | 10 |
| Example 30 | E11/20 | I(64)SA(55)SCA*(<–20)Cr | 57 | 9900 | 10 |
| Example 31 | E12/20 | I(64)SA(54)SCA*(<–20)Cr | 56 | 9800 | 10 |
| Example 32 | E13/20 | I(65)SA(53)SCA*(<–20)Cr | 42 | 4300 | 10 |
| Example 33 | E14/20 | I(64)SA(55)SCA*(<–20)Cr | 54 | 7300 | 10 |

In phase sequences, parenthesized numeral shows phase transition temperature (°C.), I stands for isotropic phase, SC* stands for chiral smectic A phase (ferroelectric phase), SA stands for smectic A phase, SCA* stands for anti-ferroelectric phase, and Cr stands for crystal phase.

Response time I: Switching time from anti-ferroelectric state to ferroelectric state (unit; µs)

Response time II: Swithcing time from ferroelectric state to anti-ferroelectric state (unit; µs)

Examples 34 and 35

The same anti-ferroelectric liquid crystal as the anti-ferroelectric liquid crystal (2A) was mixed with 10 mol % or 30 mol % of the phenyl ester compound (E10) to obtain anti-ferroelectric liquid crystal compositions. The so-obtained compositions were measured for physical properties, etc., and Table 4 shows the results.

Examples 36–38

An anti-ferroelectric liquid crystal (2B), (2C) or (2D) of the following chemical formulas was mixed with 20 mol % of the phenyl ester compound (E1) to obtain liquid crystal compositions. The so-obtained compositions were measured for physical properties, etc., and Table 4 shows the results.

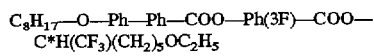

2B ($R^1=C_8H_{17}$, Y=F, $A^1=CF_3$, p=1, q=5, r=2 in the formula 2)

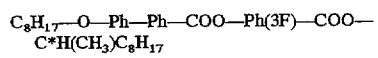

2C ($R^1=C_8H_{17}$, Y=F, $A^1=CH_3$, p=0, r=8 in the formula 2)

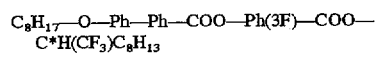

2D ($R^1=C_8H_{17}$, Y=F, $A^1=CF_3$, p=0, r=6 in the formula 2)

The observation of a conoscopic image is effective means of identifying a ferrielectric phase. The conoscopic image observation was conducted according to a piece of literature (J. Appl. Phys. 31, 793 (1992)).

On the basis of the texture observation and the conoscopic image observation by general parallel alignment cell and DSC measurement, and on the basis of the observation of an intermediate state, i.e., an observed domain having an extinguished position between a layer normal and the direction of an optic axis in a ferroelectric state, the phase sequence of the liquid crystal composition in this Example was identified. Table 5 shows the results.

The above-obtained ferrielectric liquid crystal was studied for an optical response.

A cell was prepared in the following procedures.

Glass plates with insulating film ($SiO_2$, thickness; 50 nm) and ITO electrodes were coated with polyimide (thickness; about 80 nm), and one of a pair of the glass plates was rubbed. The glass plates were attached to each other through a spacer having a particle diameter of 1.6 μm to form a test cell. The cell thickness was 2 μm. The above liquid crystal was heated until it had an isotropic phase, and the liquid crystal was injected into the test cell by capillarity. Then, the liquid crystal was gradually cooled at a rate of 1° C./minute to align the liquid crystal in parallel.

Then, the test cell was driven by applying a triangular wave voltage of ±10V, 50 mHz, to the test cell to study a change in transmission at 30° C.

TABLE 4

| | Composition | | Response time | | |
|---|---|---|---|---|---|
| | Component Molar ratio | Phase sequence | I | II | temperature |
| Ex. 34 | 2A/E10 = 90/10 | I(71)SA(66)SCA*(<−20)Cr | 75 | 5350 | 10° C. |
| Ex. 35 | 2A/E10 = 70/30 | I(53)SA(42)SCA*(<−20)Cr | 29 | 1640 | 10 |
| Ex. 36 | 2B/E1 = 80/20 | I(70)SA(62)SCA*(<−20)Cr | 45 | 1540 | 10 |
| Ex. 37 | 2C/E1 = 80/20 | I(66)SA(60)SCA*(<−20)Cr | 52 | 6200 | 10 |
| Ex. 38 | 2D/E1 = 80/20 | I(70)SA(69)SCA*(<−20)Cr | 56 | 499 | 10 |
| Liquid crystal 2B | | I(89)SA(88.6)SCA*(30)Cr *1 | | | |
| Liquid crystal 2C | | I(131)SA(114)SC*(113)SCA*(23)SX(<0)Cr *1 | | | |
| Liquid crystal 2D | | I(100)SA(108)SCA*(10)SX(0)Cr *1 | | | |

Description such as symbols in Table 4 are as defined in the notes to Table 3. SX stands for unidentified crystal phase. In lines of liquid crystals (2B, 2C and 2D), *1 shows that crystallization took place so that the response time was not measured at 10° C.

Example 39

A ferrielectric liquid crystal (3A) of the following chemical formula was mixed with 15 mol % of the phenyl ester compound (E15) obtained in Example 15 to obtain a liquid crystal composition.

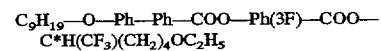

3A ($R^2=C_9H_{19}$, $Y^1$=H, $Y^2$=F, s=4, t=2 in the formula 3)

The liquid crystal composition was identified for liquid crystal phases by texture observation, conoscopic image observation, DSC (differential scanning calorimeter), and confirmation of a domain having an extinguished position between a layer normal and the direction of an optic axis in a ferroelectric state, i.e., observation of a intermediate state FI(±).

When the minimum intensity of the transmittance was taken as 0% and the maximum intensity of the transmittance was taken as 100%, the voltage at which the transmittance intensity became 90% by phase transition from a ferrielectric phase to a ferroelectric phase was defined as threshold voltage I, and the voltage at which the threshold voltage decreased to 90% by phase transition from a ferroelectric phase to a ferrielectric phase was defined as threshold voltage II.

Further, a response time was measured in the test cell. The time required for the changing of transmittance intensity by 90% under the application of a 8 V pulse voltage having a frequency of 10 Hz was defined as a response time. Table 6 shows the results.

Examples 40–43

The same ferrielectric liquid crystal as the ferrielectric liquid crystal (3A) used in Example 39 was mixed with 15 mol % of the phenyl ester compound (E4), (E5), (E8) or (E9) obtained in the above Examples to obtain liquid crystal compositions.

The liquid crystal phases of the compositions were identified, and the compositions were measured for other physical properties, in the same manner as in Example 39. Tables 5 and 6 show the results.

Example 44

The same ferrielectric liquid crystal as the ferrielectric liquid crystal (3A) used in Example 39 was mixed with 20 mol % of the phenyl ester compound (E1) obtained in Example 1 to give a liquid crystal composition.

The liquid crystal phases of the composition were identified, and the composition was measured for other physical properties, in the same manner as in Example 39. Tables 5 and 6 show the results.

TABLE 5

|  | Phase sequence | Component Molar ratio |
|---|---|---|
| Liquid crystal 3A | Cr(*1)SCγ*(89)SA(91)I |  |
| Example 39 | Cr(*1)SCγ*(73)SA(85)I | 3A/E15 = 85/15 |
| Example 40 | Cr(*1)SCγ*(70)SA(79)I | 3A/E4 = 85/15 |
| Example 41 | Cr(*1)SCγ*(70)SA(78)I | 3A/E5 = 85/15 |
| Example 42 | Cr(*1)SCγ*(72)SA(81)I | 3A/E8 = 85/15 |
| Example 43 | Cr(*1)SCγ*(71)SA(80)I | 3A/E9 = 85/15 |
| Example 44 | Cr(*1)SCγ*(64)SA(73)I | 3A/E1 = 80/20 |

Cr stands for crystal phase, SCγ* stands for ferrielectric phase, SA stands for smectic A phase, I stands for isotropic phase, and parenthesized numerals stand for transition temperatures (°C.).

(*1) shows that melting point was not detected by DSC (lower limit temperature of measurement −50° C.).

TABLE 6

|  | Threshold Voltage I (V/μm) | II (V/μm) | Response time (μsec.) | Temperature of measurement (°C.) |
|---|---|---|---|---|
| Liquid crystal 3A | 1.5 | 1.4 | 88 | 30 |
| Example 39 | 1.2 | 1.2 | 70 | 30 |
| Example 40 | 1.4 | 1.4 | 70 | 30 |
| Example 41 | 1.4 | 1.4 | 71 | 30 |
| Example 42 | 1.4 | 1.4 | 31 | 30 |
| Example 43 | 1.4 | 1.4 | 80 | 30 |
| Example 44 | 1.0 | 1.0 | 30 | 30 |

Example 45

A ferrielectric liquid crystal (3B) having the following chemical formula was mixed with 20 mol % of the phenyl ester compound (E5) obtained in Example 5 to give a liquid crystal composition.

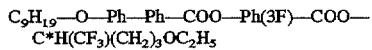

($R^2=C_9H_{19}$, $Y^1=H$, $Y^2=F$, s=3, t=2 in the formula 3)

The liquid crystal phases of the composition were identified, and the composition was measured for other physical properties, in the same manner as in Example 39. Tables 7 and 8 show the results.

Examples 46 and 47 and Referential Example 1

The same ferrielectric liquid crystal as the ferrielectric liquid crystal (3B) used in Example 45 was mixed with the phenyl ester compound (E10), (E16) or (E12) obtained in the above Examples to give liquid crystal compositions.

The liquid crystal phases of the compositions were identified, and the compositions were measured for other physical properties, in the same manner as in Example 39. Tables 7 and 8 show the results.

In Referential Example 1 (composition containing the phenyl ester compound (E12) and the ferrielectric liquid crystal (3B)), no smectic A phase was present.

TABLE 7

|  | Phase sequence | Component Molar ratio |
|---|---|---|
| Liquid crystal 3B | Cr(40)SCγ*(SA(103)I |  |
| Example 45 | Cr(*1)SCγ*(72)SA(83)I | 3B/E5 = 80/20 |
| Example 46 | Cr(*1)SCγ*(64)SA(75)I | 3B/E10 = 75/25 |
| Example 47 | Cr(*1)SCγ*(55)SA(79)I | 3B/E16 = 75/25 |
| Ref. Ex. 1 | Cr(*1)SCγ*(50)I | 3B/E12 = 75/25 |

Ref.Ex.: Referencial Examination

Descriptions in Table are as defined in the notes to Table 5.

TABLE 8

|  | Threshold Voltage I | (V/μm) II | Response time (μsec.) | Temperature of measurement (°C.) |
|---|---|---|---|---|
| Liquid crystal 3B | 1.3 | 1.2 | 101 | 30 |
| Example 45 | 1.1 | 1.0 | 58 | 30 |
| Example 46 | 1.1 | 1.1 | 23 | 30 |
| Example 47 | 1.4 | 1.4 | 61 | 30 |
| Ref. Ex. 1 | 1.3 | 1.3 | 54 | 30 |

Examples 48 and 49

The same ferrielectric liquid crystal as the ferrielectric liquid crystal (3A) used in Example 39 was mixed with 20 mol % of the phenyl ester compound (E14) or (E17) obtained in the above Examples to give liquid crystal compositions.

Examples 50 and 51

A ferrielectric liquid crystal (3C) or (3D) having the following chemical formula was mixed with 20 mol % of the phenyl ester compound (E1) obtained in Example 1, to obtain liquid crystal compositions.

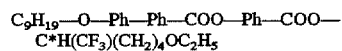

($R^2=C_9H_{19}$, $Y^1=H$, $Y^2=H$, s=4, t=2 in the formula 3)

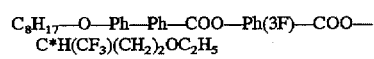

($R^1=C_8H_{17}$, $Y^1=H$, $Y^2=F$, s=2, t=2 in the formula 3)

The liquid crystal phases of the compositions obtained in Examples 48 to 51 were identified, and the compositions were measured for other physical properties, in the same manner as in Example 39. Tables 9 and 10 show the results.

TABLE 9

|  | Phase sequence | Component Molar ratio |
|---|---|---|
| Example 48 | Cr(*1)SCγ*(62)SA(72)I | 3A/E14 = 80/20 |
| Example 49 | Cr(*1)SCγ*(55)SA(72)I | 3A/E17 = 80/20 |
| Example 50 | Cr(*1)SCγ*(60)SA(80)I | 3C/E1 = 80/20 |
| Example 51 | Cr(*1)SCγ*(70)SA(85)I | 3D/E1 = 80/20 |

TABLE 9-continued

| | Phase sequence | Component Molar ratio |
|---|---|---|
| Liquid crystal 3C | Cr(41)SCγ*(95)SA(103)I | |
| Liquid crystal 3D | Cr(58)SCγ*(104)SA(108)I | |

Descriptions in Table are as defined in the notes to Table 5.

TABLE 10

| | Threshold Voltage (V/μm) I | II | Response time (μsec.) | Temperature of measurement (°C.) |
|---|---|---|---|---|
| Example 48 | 1.4 | 1.1 | 50 | 30 |
| Example 49 | 1.1 | 1.1 | 59 | 30 |
| Example 50 | 1.1 | 1.1 | 48 | 30 |
| Example 51 | 2.2 | 1.5 | 75 | 30 |
| Liquid crystal 3C | 1.8 | 1.7 | 165 | 50 |
| Liquid crystal 3D | 1.2 | 1.2 | 33 | 50 |

Example 52

A ferrielectric liquid crystal (3E) having the following chemical formula was mixed with 15 mol % of the phenyl ester compound (E1) to obtain a liquid crystal composition.

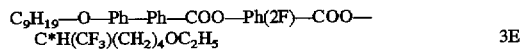

$C_9H_{19}$—O—Ph—Ph—COO—Ph(2F)—COO—$C^*H(CF_3)(CH_2)_4OC_2H_5$  3E

($R^2=C_8H_{17}$, $Y^1=F$, $Y^2=H$, s=4, t=2 in the formula 3)

Examples 53 and 54

The same ferrielectric liquid crystal as the ferrielectric liquid crystal (3A) used in Example 39 was mixed with 10 mol % of the phenyl ester compound (E10) or (E16), to obtain liquid crystal compositions.

The liquid crystal phases of the compositions obtained in Examples 52 to 54 were identified, and the compositions were measured for other physical properties, in the same manner as in Example 39. Tables 11 and 12 show the results.

TABLE 11

| | Phase sequence | Component Molar ratio |
|---|---|---|
| Example 52 | Cr(*1)SCγ*(56)SA(72)I | 3E/E1 = 85/15 |
| Liquid crystal 3E | Cr(3) SCγ*(68)SA(87)I | |
| Example 53 | Cr(*1)SCγ*(68)SA(75)I | 3A/E18 = 90/10 |
| Example 54 | Cr(*1)SCγ*(73)SA(74)I | 3A/E19 = 90/10 |

Descriptions in Table are as defined in the notes to Table 5.

TABLE 12

| | Threshold Voltage (V/μm) I | II | Response time (μsec.) | Temperature of measurement (°C.) |
|---|---|---|---|---|
| Example 52 | 0.9 | 0.9 | 61 | 30 |
| Liquid crystal 3E | 1.2 | 1.2 | 33 | 50 |
| Example 53 | 1.1 | 1.1 | 56 | 30 |
| Example 54 | 1.2 | 1.2 | 61 | 30 |

What is claimed is:

1. An anti-ferroelectric liquid crystal composition containing a phenyl ester compound of the general formula (1) and an anti-ferroelectric liquid crystal compound of the general formula (2),

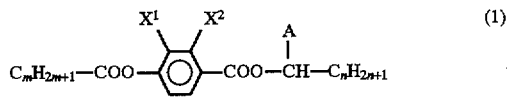

$$C_mH_{2m+1}\text{—COO—}\underset{X^1\ X^2}{\underset{|\ \ |}{\bigcirc}}\text{—COO—CH—}C_nH_{2n+1} \quad (1)$$
$$\phantom{C_mH_{2m+1}\text{—COO—}\bigcirc\text{—COO—CH—}}\overset{\overset{A}{|}}{}$$

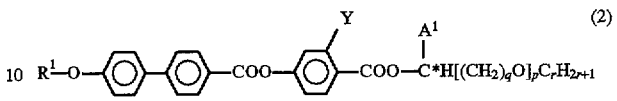

$$R^1\text{—O—}\bigcirc\text{—}\bigcirc\text{—COO—}\underset{Y}{\bigcirc}\text{—COO—}C^*H[(CH_2)_qO]_pC_rH_{2r+1} \quad (2)$$

wherein, in the general formula (1), m is an integer of 3 to 12, n is an integer of 1 to 11, both of $X^1$ and $X^2$ are hydrogen atoms, or one of $X^1$ and $X^2$ is a fluorine atom and the other is a hydrogen atom, and A is a hydrogen atom or —$CH_3$, and in the general formula (2), $R^1$ is a linear alkyl group having 4 to 12 carbon atoms, Y is a hydrogen atom or a fluorine atom and $A^1$ is —$CH_3$ or —$CF_3$, provided that when $A^1$ is —$CH_3$, p is 0 and r is an integer of 6 to 10, that when $A^1$ is —$CF_3$, p is 0 and r is an integer of 6 to 8, or that when $A^1$ is —$CF_3$, p is 1, q is an integer of 5 to 8 and r is 2 or 4.

2. The anti-ferroelectric liquid crystal composition of claim 1, wherein $R^1$ in the general formula (2) is a linear alkyl group having 6 to 8 carbon atoms.

3. The anti-ferroelectric liquid crystal composition of claim 1, wherein Y in the general formula (2) is a fluorine atom.

4. The anti-ferroelectric liquid crystal composition of claim 1, wherein, in the general formula (2), $A^1$ is —$CF_3$, p is 1 and q is 5.

5. The anti-ferroelectric liquid crystal composition of claim 1, wherein, in the general formula (2), $A^1$ is —$CF_3$, p is 1 and r is 2.

6. The anti-ferroelectric liquid crystal composition of claim 1, wherein the anti-ferroelectric liquid crystal composition contains 1 to 50 mol % of the phenyl ester compound of the general formula (1).

7. The anti-ferroelectric liquid crystal composition of claim 1, wherein the anti-ferroelectric liquid crystal composition contains 1 to 30 mol % of the phenyl ester compound of the general formula (1).

8. The anti-ferroelectric liquid crystal composition of claim 1, wherein the anti-ferroelectric liquid crystal composition exhibits an anti-ferroelectric phase in the temperature range of from 0° C. to 40° C.

9. A ferrielectric liquid crystal composition a phenyl ester compound of the general formula (1) and a liquid crystal compound having ferrielectric-phase of the general formula (3),

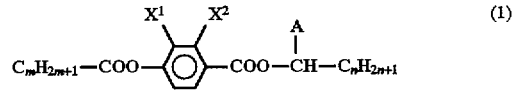

$$C_mH_{2m+1}\text{—COO—}\underset{X^1\ X^2}{\underset{|\ \ |}{\bigcirc}}\text{—COO—CH—}C_nH_{2n+1} \quad (1)$$
$$\phantom{C_mH_{2m+1}\text{—COO—}\bigcirc\text{—COO—CH—}}\overset{\overset{A}{|}}{}$$

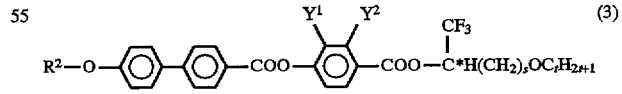

$$R^2\text{—O—}\bigcirc\text{—}\bigcirc\text{—COO—}\underset{Y^1\ Y^2}{\bigcirc}\text{—COO—}\overset{\overset{CF_3}{|}}{C^*H(CH_2)_sOC_tH_{2t+1}} \quad (3)$$

wherein, in the general formula (1), m is an integer of 3 to 12, n is an integer of 1 to 11, both of $X^1$ and $X^2$ are hydrogen atoms, or one of $X^1$ and $X^2$ is a fluorine atom and the other is a hydrogen atom, and A is a hydrogen atom or —$CH_3$, and in the general formula (3), $R^2$ is a linear alkyl group having 7 to 12 carbon atoms, both $Y^1$ and $Y^2$ are hydrogen atoms or one of $Y^1$ and $Y^2$ is a fluorine atom and the other is a hydrogen atom, s is an integer of 2 to 4 and t is an integer of 2 to 4.

10. The ferrielectric liquid crystal composition of claim 9, wherein, in the general formula (3), s is 4, t is an integer of 2 to 4 and $R^2$ is a linear alkyl group having 7 to 12 carbon atoms.

11. The ferrielectric liquid crystal composition of claim 9, wherein, in the general formula (3), s is 3, t is an integer of 2 to 4 and $R^2$ is a linear alkyl group having 9 to 12 carbon atoms.

12. The ferrielectric liquid crystal composition of claim 9, wherein, in the general formula (3), s is 2 and $R^2$ is a linear alkyl group having 8 or 9 carbon atoms.

13. The ferrielectric liquid crystal composition of claim 9, wherein, in the general formula (3), s is 2 and t is 2.

14. The ferrielectric liquid crystal composition of claim 9, wherein the ferrielectric liquid crystal composition contains 1 to 40 mol % of the phenyl ester compound of the general formula (1).

15. The ferrielectric liquid crystal composition of claim 9, wherein the ferrielectric liquid crystal composition contains 10 to 30 mol % of the phenyl ester compound of the general formula (1).

16. The ferrielectric liquid crystal composition of claim 9, wherein the ferrielectric liquid crystal composition exhibits a ferrielectric phase in the temperature range of from 0° C. to 40° C.

17. The ferrielectric liquid crystal composition of claim 9, wherein the ferrielectric liquid crystal composition has a threshold voltage, at which the ferrielectric liquid crystal composition changes from a ferrielectric phase to a ferroelectric phase, of 5 V/μm or smaller.

18. The ferrielectric liquid crystal composition of claim 9, wherein the ferrielectric liquid crystal composition has a threshold voltage, at which the ferrielectric liquid crystal composition changes from a ferrielectric phase to a ferroelectric phase, of 3 V/μm or smaller.

* * * * *